United States Patent [19]

Pickart

[11] Patent Number: 5,214,032
[45] Date of Patent: May 25, 1993

[54] GHL-CU PHARMACEUTICAL COMPOSITIONS AND COMPOUNDS

[75] Inventor: Loren R. Pickart, Bellevue, Wash.

[73] Assignee: ProCyte Corporation, Bellevue, Wash.

[21] Appl. No.: 899,378

[22] Filed: Jun. 16, 1992

Related U.S. Application Data

[63] Continuation-in-part of Ser. No. 442,440, Sep. 22, 1989, which is a continuation-in-part of Ser. No. 48,444, May 11, 1987, abandoned, which is a continuation-in-part of Ser. No. 699,824, Feb. 8, 1985, Pat. No. 4,665,054.

[51] Int. Cl.$^5$ .................. A61K 37/02; C07K 7/06
[52] U.S. Cl. ........................... 514/16; 514/6; 514/17; 514/18; 530/331; 530/329
[58] Field of Search .............. 530/331, 329; 514/6, 514/18, 16, 17

[56] References Cited

U.S. PATENT DOCUMENTS

| | | | |
|---|---|---|---|
| 3,194,732 | 9/1965 | Neuhauser | 514/18 |
| 3,551,554 | 12/1970 | Herschler | 514/18 |
| 3,558,770 | 1/1971 | Gordon et al. | 514/18 |
| 3,758,682 | 9/1973 | Huber et al. | 514/18 |
| 3,767,784 | 10/1973 | Gluck | 514/18 |
| 3,832,338 | 8/1974 | Huber et al. | 514/18 |
| 4,022,888 | 5/1977 | Huber et al. | 514/18 |
| 4,167,945 | 9/1979 | Gottlieb | 514/18 |
| 4,177,261 | 12/1979 | Dietze et al. | 514/18 |
| 4,263,428 | 4/1981 | Apple et al. | 514/18 |
| 4,287,184 | 9/1981 | Young | 514/18 |
| 4,440,788 | 4/1984 | Terayama et al. | 514/18 |
| 4,665,054 | 5/1987 | Pickart | 514/18 |

OTHER PUBLICATIONS

Pickart et al., "Growth-Modulating Tripeptide (glycyl-histidylysine): Association with Copper and Iron in Plasma and Stimulation of Adhesive and Growth of Hepatoma Cells in Culture by Tripeptide-Metal Ion Complexes," *J. Cell. Physiol.*, 102(2):129-139, 1980. (Cited in Chem. Abstracts 93:1155m, 1980).

Williams et al., "Glycyl-L-Histidyl-L-Lysine, a Growth Promoting Factor for Human Cells," *Cytobios*, 27(105):19-25, 1980. (Cited in Chem. Abstracts 94:25451b, 1981).

Mochida Pharmaceutical Co., Ltd., "Antiinflammatory Injections Containing Superoxide Dismutase," Jpn. Kokai Tokkyo Koho, 81 07,720 Jan. 27, 1981. (Cited in Chem. Abstracts, vol. 94: 145386f, 1981).

Kwa, "Glycyl-L-Histidyl-L-Lysine Synthesis of Analogs and NMR Studies," Ph.D. Thesis, University of Washington, 1983.

Loker, "Synthesis of Blood Serum Peptide Cell Growth Factors," Ph.D. Thesis, University of Washington 1980.

Pickart, "The Biological Effects and Mechanism of Action of the Plasma Tripeptide Glycyl-L-Histidyl-L-Lysine," *Lymphonkines*, 8:425–446, 1983.

Poole et al., "Stimulation of Rat Peritoneal Mast Cell Migration by Tumor-Derived Peptides," *Cancer Research*, 43:5857–5861, 1983.

Raju et al., "Ceruloplasmin, Copper Ions, and Angiogenesis," *JUNCI*, 69(5):1183–1188, 1982.

Freedman et al., "Structure of the Glycyl-L-Histidyl-L-Lysine-Copper(II) Complex in Solution," *Biochemistry*, 21:4540–4544, 1982.

Kwa et al., "PMR Studies of CU(II) and Zn(II) Interaction with Glycyl-L-Histidyl-L-Lysine and Related Peptides," *Peptides: Structure and Function*, 8, pp. 805–808, 1983.

Perkins et al., "The Structure of a Copper Complex and the Growth Factor Glycyl-L-Histidyl-L-Lysine at 1.1 A Resolution," *Inorganica Chimica Acta*, 82, pp. 93–99, 1984.

(List continued on next page.)

Primary Examiner—Lester L. Lee
Attorney, Agent, or Firm—Seed and Berry

[57] ABSTRACT

Methods and compositions for (a) stimulating the growth of hair in warm-blooded animals, (b) increasing subcutaneous fat in warm-blooded animals, and (c) increasing the density of hair follicles in warm-blooded animals are disclosed. The methods utilize an effective amount of a composition comprising a derivative of GHL-Cu.

4 Claims, 2 Drawing Sheets

OTHER PUBLICATIONS

Kimoto et al., "Enhancement of Antitumor Activity of Ascorbate Against the Copper: Glycylglycylhistidine Complex," *Cancer Research,* 43, pp. 824–828, 1963.

Sorenson, "Copper Complexes: A Physiological Approach to Treatment of Chronic Diseases," *Comprehensive Therapy,* 11(4):49–64, 1985.

Pickart et al., "Inhibition of the Growth of Cultured Cells and an Implanted Fibrosarcoma by Aroylhydrazone Analogs of the Gly-Hi-Lys-Cu(II) Complex," *Biochem. Pharmacol.,* 32(24), pp. 3868–3871, 1983.

Pickart et al., "Growth-Modulating Plasma Tripeptide May Function by Facilitating Copper Uptake Into Cells," *Nature,* 288, pp. 815–717, 1980.

Natural Healing Annual 1986, p. 38 (Edit M. Bricklin, Prevention Magazine, Rodale Press, Emmaus, Pa.).

Pickart et al., "A Synthetic Tripeptide which Increases Survival of Normal Liver Cells, and Stimulates Growth in Hepatoma cells," *Biochem. Biophys. Res. Commun.,* 54(2), pp. 526–526, 1973.

Aonuma et al., "Studies on Anti-Ulverogenic Protein in Inflamed Rabbit Skin Tissues," *Yakugaku Zasshi* 104(4):362–73, 1984.

Downey et al., "Acceleration of Wound Healing using GHL-Cu(II)," *Surgical Forum* 36:573–75, 1985.

Pckart et al., "A Human Plasma Growth Factor with Superoxide Dismutase-like and Wound-healing Properties," Superoxide Dim. Chem. Biol. Med. Proc. Int. Conf. 4th 1985 (Pub. 1986), 555–57 (Cited in *Chem. Abstracts* 106:13579c).

Frater-Schroder et al., "Tumor Necrosis Factor Type a Potential Inhibitor of Endothelial Cell Growth in vitro is angiogenic in vivo," *Proc. Natl. Acad. Sci. USA* 34:5277–81, 1987.

Pickart, "The Use of Glycylhistidyllysine in Culture Systems," In Vitro 17(6):459–66, 1981.

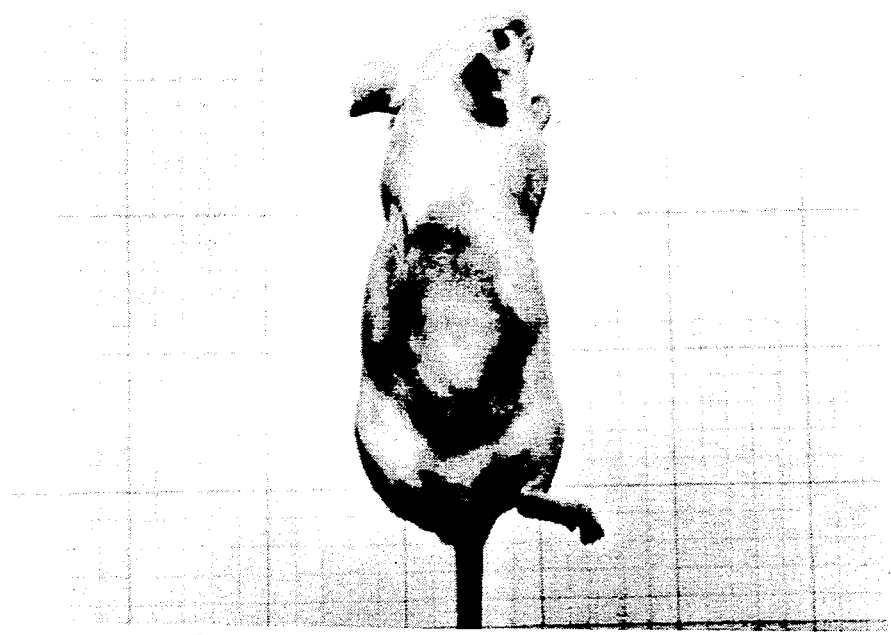
FIG. 1
FIG. 2

FIG. 3A
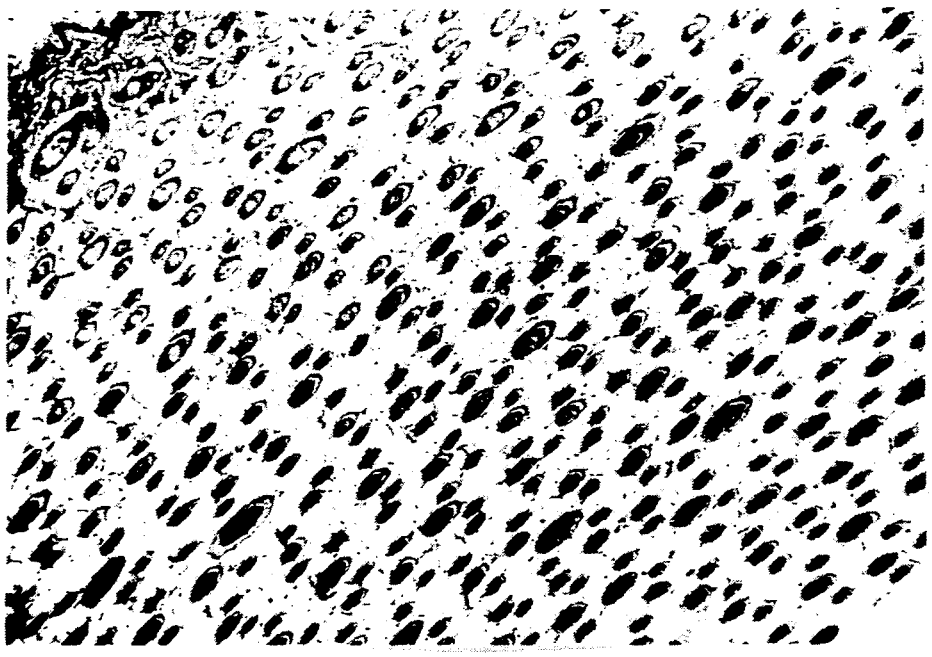
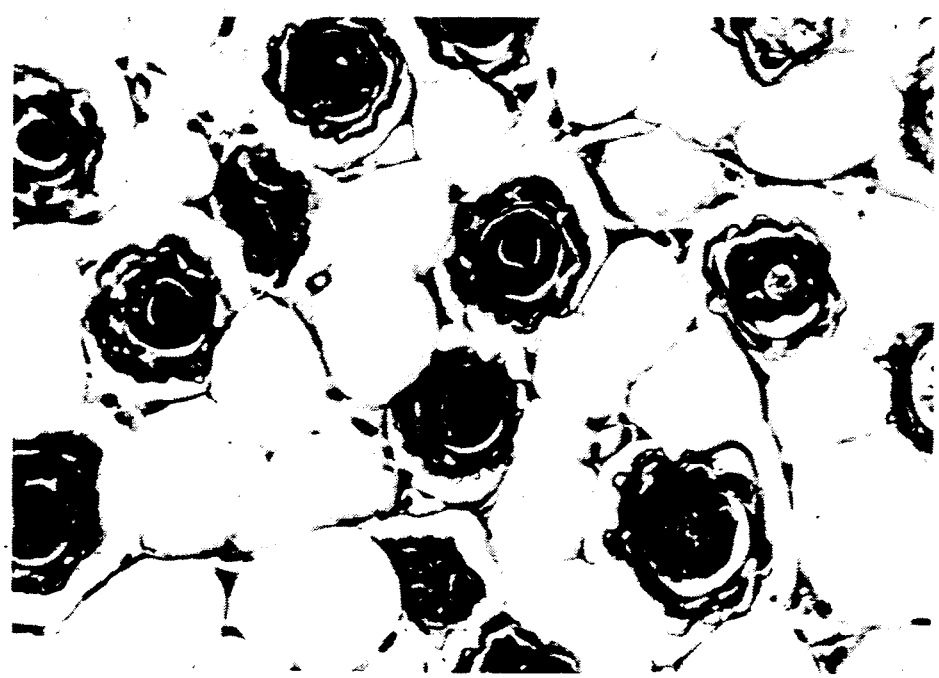
FIG. 3B

GHL-CU PHARMACEUTICAL COMPOSITIONS AND COMPOUNDS

Cross-Reference to Related Applications

This application is a continuation of U.S. application Ser. No. 442,440, filed Sep. 22, 1989; which is a continuation of U.S. application Ser. No. 048,444, filed May 11, 1987, now abandoned; which is a continuation-in-part of U.S. application Ser. No. 699,824, filed Feb. 8, 1985, issued as U.S. Pat. No. 4,665,054.

TECHNICAL FIELD

The present invention relates to the stimulation of hair growth in general, and more specifically, to the use of derivatives of glycyl-L-histidyl-L-lysine: copper(II) (GHL-Cu) in part, in the stimulation of hair growth in warm-blooded animals.

BACKGROUND ART

While attempts to grow hair date back approximately 5,000 years to ancient Engyptian formulas, and while in developed countries, approximately 50–100 million persons suffer from cosmetic hair loss, there has been relatively little significant the growth of hair. For instance, selected "hair growth" preparations which have been proposed include compositions of vitamins E, $B_2$, and $B_6$, crude drug extracts, karotin-solubilizing agents, germacides, and scalp-stimulating agents, all alleged to stimulate the growth of hair.

Another traditional treatment for the loss of hair has been hair transplantation. Briefly, plugs of skin containing hair are transplanted from areas of the scalp where the hair was growing to bald areas. This procedure is a costly one in addition to being time-consuming and relatively painful. Other non-drug approaches include ultra-violet radiation and exercise therapy.

Traditionally, one of the most common approaches to stimulating their growth has been in the area of drug therapy. However, the use of drugs in this regard has met with limited success. One of the most promising compositions for stimulating the growth of hair is disclosed by Upjohn in U.S. Pat. No. 4,596,812, which describes the use of a substance known as "Minoxidil." However, while the results generated through the use of Minoxidil have heretofore appeared promising, there is still a need in the art for improved compositions capable of stimulating the growth of hair in warm-blooded animals. The present invention fulfills this need, while further providing other related advantages.

DISCLOSURE OF THE INVENTION

Briefly stated, the present invention discloses a pharmaceutical composition for use within a method for stimulating the growth of hair in warm-blooded animals. The method generally comprises administering to the animal a stimulatory amount of a derivative of GHL-Cu having the general formula:

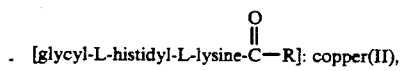

wherein R is selected from the group consisting of alkyl moieties containing from one to eighteen carbon atoms, aryl moieties containing from six to twelve carbon atoms, alkoxy moieties containing from one to 18 carbon atoms, and aryloxy moieties containing from six to twelve carbon atoms, or where R is L-prolyl-L-valyl-L-phenylalanyl-L-valine or L-valyl-L-phenylalanyl-L-valine. Within a preferred embodiment, the alkyl moiety is an unbranched chain, such as an N-octyl moiety. Further, the alkyl moiety may be an N-stearyl moiety or an N-palmityl moiety.

Another aspect of the present invention, a method for increasing subcutaneous fat in warm-blooded animals, is disclosed. The method comprises administering to the animal an effective amount of a composition including a derivative of CHL-Cu having the general formula:

wherein R is selected from the group consisting of alkyl moieties containing from one to eighteen carbon atoms, aryl moieties containing from six to twelve carbon atoms, alkoxy moieties containing from one to twelve carbon atoms, and aryloxy moieties containing from six to 18 carbon atoms, or where R is L-prolyl-L-valyl-L-phenylalanyl-L-valine or L-valyl-L-phenylalanyl-L-valine.

Within yet another aspect of the present invention, a method for increasing the density of hair follicles in warm-blooded animals is disclosed. The method generally comprises administering to the animal an effective amount of a composition comprising a derivative of CHL-Cu having the general formula:

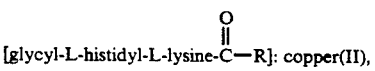

wherein R is selected from the group consisting of alkyl moieties containing from one to eighteen carbon atoms, aryl moieties containing from six to twelve carbon atoms, alkoxy moieties containing from one to 18 carbon atoms, and aryloxy moieties containing from six to twelve carbon atoms, or where R is L-prolyl-L-valyl-L-phenylalanyl-L-valine or L-valyl-L-phenylalanyl-L-valine.

In addition to the derivatives described above, other chemical modifications could be made to alter the biological activity of the derivatives of the present invention. For instance, glycine may be replaced by a variety of other small amino acids, including alanine, serine and valine. Further, the copper(II) binding affinity of the molecule could be increased by addition of an N-terminal amino acid such as glycine to convert glycyl-L-histidyl-L-lysine to glycyl-L-glycyl-L-histidyl-L-lysine. In addition, glycine could be added to a derivative as described above to create the corresponding tetrapeptide.

The compositions described herein may be injected intradermally or applied topically, and are rendered suitable for administration to warm-blooded animals for the purposes of the present invention by combining the derivative with a vehicle which adapts the composition for either intradermal injection or topical application to a warm-blooded animal. Suitable vehicles include physiological saline.

Other aspects of the present invention will become evident upon reference to the following detailed description and attached drawings.

BRIEF DESCRIPTION OF THE DRAWINGS

FIG. 1 is a photograph illustrating the stimulation of hair growth through the use of a derivative of the present invention.

FIG. 2 is a photograph illustrating the stimulation of hair growth around a surgical defect utilizing a derivative of the present invention.

FIGS. 3A and 3B are microphotographs of a control area and an area of enhanced hair growth, respectively, illustrating an increase in the density of hair follicles embedded in a heavy field of large, subcutaneous fat cells.

BEST MODE FOR CARRYING OUT THE INVENTION

As described herein, various derivatives of GHL-Cu may be used to stimulate the growth of hair in warm-blooded animals. In addition, these derivatives can be tailored to increase their fat solubility, resulting in a form of the molecule which is more useful in a formulation of pharmaceutical creams and gels. The derivatives of the present invention are described in detail in pending U.S. patent application Nos. 699,824 and 040,460, which applications are hereby incorporated by reference. The derivatives of the present invention may be prepared by esterification, by the removal of a water molecule, or by the addition of a group (either an alcohol such as octanol, methanol, benzol alcohol or $NH_3$) to the carboxylic acid terminus of GHL, resulting in the formation of the more lipophilic derivative. This increases fat solubility by (1) removal of the electric charge associated with the carboxylic acid group and (2) the introduction of hydrophilic groups into the molecule.

The overall chemical reaction in this transformation may be characterized as:

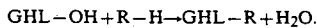
GHL—OH+R—H→GHL—R+H$_2$O.

In practice, the reaction is most readily carried out by adding the R group to the amino acid lysine prior to the combination of lysine with the other two amino acids to GHL. After the formation and isolation of GHL-R, the copper(II) is chelated to the molecule to form the bioactive complex.

The overall reaction to form the more lipophilic derivatives of GHL-Cu may be characterized:

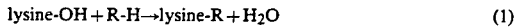
lysine-OH + R-H → lysine-R + H$_2$O   (1)

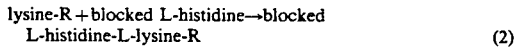
lysine-R + blocked L-histidine → blocked
L-histidine-L-lysine-R   (2)

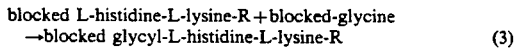
blocked L-histidine-L-lysine-R + blocked-glycine
→ blocked glycyl-L-histidine-L-lysine-R   (3)

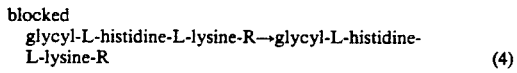
blocked
glycyl-L-histidine-L-lysine-R → glycyl-L-histidine-
L-lysine-R   (4)

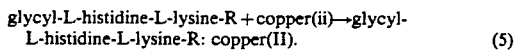
glycyl-L-histidine-L-lysine-R + copper(ii) → glycyl-
L-histidine-L-lysine-R: copper(II).   (5)

Within preferred embodiments, the derivative of GHL and copper are present in a 1:1 or 2:1 ratio.

As noted above, the derivatives of the present invention are useful in stimulating the growth of hair in warm-blooded animals. While one of the characteristics associated with male pattern baldness is the severe diminution of hair follicles, use of the derivatives as described herein results in increased adipocyte formation, which is spatially and temporally linked with hair follicle formation, and is an integral phase of hair follicle formation (Hausman et al., *Am. J. Anat.* 161:85–100, 1981). The results of the use of the derivatives as described herein are illustrated in FIGS. 3A and 3B, which are microphotographs of a control area and an area of enhanced hair growth, respectively. More specifically, as shown in FIG. 3B, the hair follicles 12 (dark objects) are embedded in a heavy field of large, subcutaneous fat cells 14 (white rounded cells) surrounded by blood capillaries 16.

The enhancement of subcutaneous fat in areas associated with increased hair growth is highly significant. Male pattern baldness is intimately associated with a dramatic reduction in the amount of subcutaneous fat associated with hair follicles that are nonproductive. Conversely, during periods of rapid hair growth in mammals, the subcutaneous fat content increase two- to threefold.

The derivatives of the present invention have clinical use in at least two primary areas: (1) the direct stimulation of hair growth in persons with hair loss, (2) the stimulation of hair transplants, and (3) increasing the subcutaneous fat content.

Within the present invention, it is generally preferred to administer the derivatives described herein intradermally in the center of the area to be treated, along with a suitable vehicle in a concentration of approximately 50 micrograms of derivative per a 1 ml of vehicle. It is preferable to use a dosage of approximately 9 micrograms per $cm^2$ of area to be treated, although dosages greater than 9 micrograms/$cm^2$, up to approximately 40 micrograms/$cm^2$, may be used. Suitable vehicles in this regard include saline. When used in the form of a cream or gel and applied topically, it is useful to add a suitable penetrating agent, such as DMSO, to the composition.

To summarize the examples which follow, Example I illustrates the synthesis of glycyl-L-histidyl-L-lysine benzyl ester: copper(II). Example II demonstrates the synthesis of glycyl-L-histidyl-L-lysine n-octyl ester: copper(II). Example III illustrates (A) the synthesis of glycyl-L-histidyl-L-lysine n-stearyl ester: copper(II), and (B) its synthesis by an alternative procedure. Based upon either procedure, one skilled in the art could substitute n-palmityl alcohol (16 carbons) for the n-stearyl alcohol (18 carbons) to yield glycyl-L-histidyl-L-lysine n-stearyl ester: copper(II). Example IV illustrates the synthesis of glycyl-L-histidyl-L-lysyl-L-propyl-L-valyl-L-phenylalanyl-L-valine: copper(II) and glycyl-L-histidyl-L-lysyl-L-valyl-L-phenylalanyl-L-valine: copper(II). Example V illustrates the hair growth stimulating activity of a preferred derivative of the present invention.

The following examples are offered by way of illustration and not by way of limitation.

EXAMPLES

Sources of chemicals. Chemicals and peptide intermediates utilized in the following examples may be purchased from the following suppliers: Sigma Chemical Co. (St. Louis, Mo.); Peninsula Laboratories (San Carlos, Calif.); Aldrich Chemical Co. (Milwaukee, Wis.); Vega Biochemicals (Tucson, Ariz.); Pierce Chemical Co. (Rockford, Ill.); Research Biochemicals (Cleveland, Ohio); Van Waters and Rogers (South San Francisco, Calif.) Bachem, Inc. (Torrance, Calif.).

EXAMPLE I

Synthesis of glycyl-L-histidyl-L-lysine benzyl ester: copper(II)

$N^e$-benzyloxycarbonyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated. The product, $N^{im}$-benzyloxycarbonyl-L-histidyl-$N^e$-benzoylcarbonyl-L-lysine benzyl ester, was coupled to t-butyloxycarbonylglycine with dicyclohexylcarbodiimide as a coupling agent. Blocking groups were removed by catalytic hydrogenation using 10% palladium on carbon in glacial acetic acid. After lyophilization, the product, glycyl-L-histidyl-L-lysine benzyl ester, was dissolved in water and purified by ion-exchange chromatography on Dowex 50 X-4 cation-exchange resin and elution with 0.1M ammonium hydroxide, the eluate being immediately neutralized with acetic acid. A further passage through an anion-exchange column BioRex 63 at neutral pH removed breakdown products with free carboxylic acid groups.

The glycyl-L-histidyl-L-lysine benzyl ester was dissolved in water with equimolar copper acetate added. The pH was raised to neutrality with sodium hydroxide. The solution was centrigured at 20,000×g for 1 hour at 3° C. to remove poorly water-soluble material. The supernatant was lyophilized to obtain glycyl-L-histidyl-L-lysine benzyl ester: copper(II).

EXAMPLE II

Synthesis of glycyl-L-histidyl-L-lysine n-octyl ester: copper(II)

A mixture of $N^e$-benzyloxycarbonyl-L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitated solid was added to 50 ml potassium carbonate solution and 50 ml dichloromethane. After extraction, the layers were separated and the organic phase washed with water and brine, then dried with anhydrous magnesium sulfate. Filtration, evaporation and purification by flash column chromatography gave n-octyl $N^e$-benzyloxycarbonyl-L-lysinate. The product was dissolved in tetrahydrofuran and mixed with $N^a$-t-butyloxycarbonyl-L-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium surfate. Filtration, evaporation and purification by flash column chromatography gave n-octyl $N^a$-t-butyloxycarbonyl-$N^{im}$-benzoyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformate, N-methylmorpholine and benzyloxycarbonylglycine were added to form n-octyl benzyloxycarbonylglycyl-$N^{im}$-benzyloxycarbonyl-L-histidyl-$N^e$-benzyloxycarbonyl-L-lysinate. This was dissolved in glacial acetic acid and hydrogenated overnight.

The resultant n-octyl ester of glycyl-L-histidyl-L-lysine was converted to the copper-complex by the addition of an equimolar quantity of copper diacetate. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine n-octyl ester: copper(II).

EXAMPLE III

A. Synthesis of glycyl-L-histidyl-L-lysine n-stearyl ester: copper(II)

A mixture of $N^e$-benzyloxycarbonyl-L-lysine, n-stearyl alcohol, benzene, and p-toluenesulfonic acid monohydrate was refluxed overnight using a Dean-Start trap to remove water. After cooling, dry propyl ether was added to increase the total volume sixfold. The product was allowed to precipitate at 0° C. overnight and filtered. A portion of the filtrate was added to 50 ml potassium carbonate and 50 ml dichloromethane. After extraction, the layers were separated, and the organic phase was washed with water and brine, then dried with anhydrous magnesium sulfate. Filtration, evaporation and purification by flash column chromatography gave n-stearyl $N^e$-benzyloxycarbonyl-L-lysinate. The product was dissolved in tetrahydrofuran and mixed with $N^a$-t-butyloxycarbonyl-$N^{im}$-benzyloxycarbonyl-L-histidine and isobutyl chloroformate and N-methylmorpholine. After evaporation, water and propyl acetate were added and the product was extracted into the organic phase, then dried with anhydrous magnesium sulfate. Filtration, evaporation and purification by flash column chromatography gave n-stearyl $N^a$-t-butyloxycarbonyl-$N^{im}$-benzoyloxycarbonyl-L-histidyl-$N^e$-benzyloxycarbonyl-L-lysinate.

The product was dissolved in 50% trifluoroacetic acid in dichloromethane for 30 minutes, then evaporated, forming n-stearyl $N^{im}$-benzyloxycarbonyl-L-histidyl-$N^e$-benzyloxycarbonyl-L-lysinate, which was dissolved in tetrahydrofuran, isobutyl chloroformate, N-methylmorpholine and benzyloxycarbonylglycine to form n-stearyl benzyloxy-carbonylglycyl-$N^{im}$-benzoyloxycarbonyl-L-histidyl-$N^e$-benzyl-oxycarbonyl-L-lysinate, which was dissolved in tetrahydrofuran, isobutyl chloroformate, N-methylmorpholine and benzyloxycarbonylglycine to form n-stearyl benzyloxy-carbonylglycyl-$N^{im}$-benzyloxycarbonyl-L-histidyl-$N^e$-benzyl-oxycarbonyl-L-lysinate. The product was dissolved in 50% trifluoroacetic acid in dichloromethane for 30 minutes, then evaporated, forming n-stearyl ester glycyl-L-histidyl-L-lysine.

The resultant molecule, glycyl-L-histidyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

B. Alternative synthesis of glycyl-L-histidyl-L-lysine n-stearyl ester: copper(II)

N(ε)-benzyloxycarbonyl-L-lysine, n-stearyl alcohol, p-toluenesulfonic acid monohydrate, and benzene are refluxed together using a Dean-Stark trap to azeotropically remove the evolved water. After cooling to room temperature and then adding dry ethyl ether, n-stearyl N(ε)-benzyloxycarbonyl-L-lysinate p-toluenesulfonate salt is collected by filtration, treated with 2M aqueous potassium bicarbonate solution, and extracted into dichloromethane. Evaporation give the free amine, which is redisolved in dry tetrahydrofuran (THF) and added to a stirring solution of N(α)-t-butyloxycarbonyl-N(im)-benzyloxy-carbonyl-L-histidine, N-methylmorpholine, and isobutyl chloroformate in dry THF at −15° C. The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine and isobutyl chloroformate in dry THF at −15° C. The formed, fully protected tripeptide ester is totally deblocked by treatment with hydrogen gas in glacial acetic acid at room temperature in the presence of Pd-C catalyst. Filtration, evaporation and purification on a microcrystalline cellulose column followed by lyophilization give the desired tripeptide ester as its triacetate salt.

The resultant molecule, glycyl-L-histidyl-L-lysine n-stearyl ester, was converted to the copper-complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

EXAMPLE IV

Synthesis of glycyl-L-histidyl-L-lysyl-L-prolyl-L-valyl-L-phenylalanyl-L-valine: copper(II) and of glycyl-L-histidyl-L-lysyl-L-valyl-L-phenylalanyl-L-valine: copper(II)

These peptides are synthesized by standard solid-phase methods common to the peptide field (J. Stewart and J. Young, *Solid Phase Peptide Synthesis*, Pierce Chemical Co., 1984). Briefly stated, Boc-Val-O-Resin was sequentially coupled with other blocked amino acids using dicyclohexylcarbodiimide as a reaction agent. Protected amino acids, resins for solid-phase synthesis, and coupling agents were obtained from Peninsula Laboratories, San Carlos, Calif. Blocked amino acids are added in sequential order to obtain the desired peptide. The final peptide is deblocked using hydrogen fluoride. The final peptide is dissolved in 0.5% acetic acid and purified by passage through a Sephadex G-15 column (Pharmacia). Addition of equimolar cupric acetate, followed by lyophilization, produces the active molecule.

EXAMPLE V

Use of glycyl-L-histidyl-L-lysine n-octyl ester: copper(II) to stimulate hair growth

A. Stimulation of hair growth in normal skin

In order to demonstrate the stimulation of hair growth in warm-blooded animals, the backs of mice were shaved on day 1 using an electric shaver. Subsequently, a single dose of 50 micrograms of glycyl-L-histidyl-L-lysine n-octyl ester: Cu(II) was infiltrated under the skin in eight mice. As shown in FIG. 1, by day 7 there was a markedly accelerated growth of hair around the injection area in all of the mice.

In some regions of enhanced hair growth, increased follicle densities were observed, along with increased amounts of subcutaneous fat.

B. Stimulation of hair growth around a closing wound

Reestablishment of hair growth is a normal part of healing. As shown in FIG. 2, the GHL-Cu derivatives described herein may be used to stimulate the growth of hair around a surgical defect. The enhanced hair growth after healing was well advanced (7 to 10 days) and spread outward from the injected area. The maximal differential effect (vs. control) was observed approximately 22 days after injection.

These examples demonstrate that the stimulation of hair growth is observed both in normal skin and in newly healing regions utilizing the derivatives of the present invention.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A pharmaceutical composition suitable for administration to warm-blooded animals for stimulating the growth of hair, comprising:
   a derivative of GHL-Cu having the general formula:

copper(II)

wherein R is L-prolyl-L-valyl-L-phenylananyl-L-valine or L-valyl-L-phenylananyl-L-valine; and
   a vehicle which adapts said composition for intradermal injection or topical application to a warm-blooded animal.

2. The composition of claim 1 wherein the ratio of the derivative of GHL to Cu is 2:1.

3. A compound having the following general formula:

copper(II)

wherein R is L-prolyl-L-valyl-L-phenylananyl-L-valine or L-valyl-L-phenylananyl-L-valine.

4. The compound of claim 3 wherein the ratio of the derivative of GHL to Cu is 2:1.

* * * * *

UNITED STATES PATENT AND TRADEMARK OFFICE
CERTIFICATE OF CORRECTION

PATENT NO. : 5,214,032
DATED : May 25, 1993
INVENTOR(S) : Loren R. Pickart

It is certified that error appears in the above-identified patent and that said Letters Patent is hereby corrected as shown below:

In column 8, claim 1, line 46, please delete "copper(II)" and substitute therefor --[glycyl-L-histidyl-L-lysine-R]:copper(II)--.

In column 8, claim 3, line 57, please delete "copper(II)" and substitute therefor --[glycyl-L-histidyl-L-lysine-R]:copper(II)--.

Signed and Sealed this

Twenty-second Day of March, 1994

BRUCE LEHMAN

Attest:

Attesting Officer       Commissioner of Patents and Trademarks